United States Patent
Rallapalli et al.

(10) Patent No.: US 10,781,153 B2
(45) Date of Patent: Sep. 22, 2020

(54) RECOVERY OF ETHYL HEXANOL FROM RECYCLE STREAMS IN 2-ETHYL HEXANOL PROCESS

(71) Applicant: SABIC Global Technologies B.V., Bergen op Zoom (NL)

(72) Inventors: Jagan Mohan Rallapalli, Riyadh (SA); Ameen Ghamdi-Al, Riyadh (SA); Somak Paul, Riyadh (SA)

(73) Assignee: SABIC GLOBAL TECHNOLOGIES B.V., Bergen op Zoom (NL)

( * ) Notice: Subject to any disclaimer, the term of this patent is extended or adjusted under 35 U.S.C. 154(b) by 0 days.

(21) Appl. No.: 16/761,748

(22) PCT Filed: Nov. 13, 2018

(86) PCT No.: PCT/IB2018/058925
§ 371 (c)(1),
(2) Date: May 5, 2020

(87) PCT Pub. No.: WO2019/097403
PCT Pub. Date: May 23, 2019

(65) Prior Publication Data
US 2020/0262772 A1    Aug. 20, 2020

Related U.S. Application Data

(60) Provisional application No. 62/588,571, filed on Nov. 20, 2017.

(51) Int. Cl.
*C07C 29/84* (2006.01)
*C07C 45/50* (2006.01)
*C07C 45/78* (2006.01)

(52) U.S. Cl.
CPC .............. *C07C 29/84* (2013.01); *C07C 45/50* (2013.01); *C07C 45/78* (2013.01)

(58) Field of Classification Search
CPC .......... C07C 29/84; C07C 45/50; C07C 45/78
See application file for complete search history.

(56) References Cited

U.S. PATENT DOCUMENTS

| | | | |
|---|---|---|---|
| 4,138,588 A | 2/1979 | Tummes et al. | |
| 4,684,750 A | 8/1987 | Kessen et al. | |

(Continued)

FOREIGN PATENT DOCUMENTS

| | | |
|---|---|---|
| CN | 104961624 B | 8/2016 |
| KR | 100804821 | 2/2008 |

OTHER PUBLICATIONS

International Search Report and Written Opinion from PCT/IB2018/058925 dated Feb. 21, 2019, 11 pages.

*Primary Examiner* — Jafar F Parsa
(74) *Attorney, Agent, or Firm* — Norton Rose Fulbright US LLP

(57) ABSTRACT

A method of recovering 2-ethyl hexanol (2-EH) from crude alcohol that includes the 2-ethyl hexanol, 2-ethyl, 3-propyl acrolein (EPA), and 2-ethylhexanal (EHA) is disclosed. The crude alcohol stream is first separated into a first stream of primarily 2-EH, a second stream of primarily EPA and 2-EH collectively, and a third stream of primarily 2-EH and EHA collectively. The second stream and the third stream are combined to form a combined stream. The combined stream is processed further to form a first product stream comprising primarily 2-EH and a second product stream comprising primarily, 2-EH, EHA, and EPA collectively.

20 Claims, 3 Drawing Sheets

(56) References Cited

U.S. PATENT DOCUMENTS 9,511,306 B2 12/2016 Lee et al.
2016/0075621 A1* 3/2016 Hashmi .................. C07C 45/74
560/99

* cited by examiner

RECOVERY OF ETHYL HEXANOL FROM RECYCLE STREAMS IN 2-ETHYL HEXANOL PROCESS

CROSS REFERENCE TO RELATED APPLICATIONS

This application is a national phase application under 35 U.S.C. § 371 of International Application No. PCT/IB2018/058925 filed Nov. 13, 2018, which claims priority to U.S. Provisional Patent Application No. 62/588,571 filed Nov. 20, 2017. The entire contents of each of the above-referenced disclosures is specifically incorporated by reference herein without disclaimer.

FIELD OF INVENTION

The present invention generally relates to the production of 2-ethyl hexanol. Specifically, the present invention relates to the production of crude alcohol and recovery of 2-ethyl hexanol from the crude alcohol.

BACKGROUND OF THE INVENTION 2-ethyl hexanol (2-EH) is a high boiling point, low volatility liquid used as a solvent, a fragrance, and precursor material for the production of plasticizers, lubricants, paints, and coatings. 2-EH can be produced by a series of reactions. First, synthesis gas and propylene are reacted with each other to produce butyraldehyde. Second, the butyraldehyde is then converted to 2-ethyl, 3-propyl acrolein (EPA) by simultaneous aldolisation and dehydration. Third, 2-EH is produced by hydrogenation of EPA in two steps. In the first hydrogenation step, EPA is partially hydrogenated to produce 2-ethylhexanal (EHA). In the second hydrogenation step, the EHA is further hydrogenated to produce 2-EH in a crude alcohol product. It should be noted that, typically, not all of the EPA is converted to EHA and not all the EHA is converted to 2-EH.

Thus, the crude alcohol product contains mainly 2-EH, but also contains EHA, EPA, butanol, heavies, and water. Thus, in order to prepare the 2-EH for market, a product purification unit purifies the crude alcohol. The purification unit can contain one or more distillation columns for separating the 2-EH from the various other components in the crude alcohol. The purification unit produces a first stream comprising primarily 2-EH product, a second stream comprising primarily 2-EH and EHA, a third stream comprising primarily EPA and 2-EH, a fourth stream comprising primarily lights discharged as waste liquid fuel, and a fifth stream comprising heavies discharged as waste liquid fuel.

FIG. 1 shows prior art system 10 for producing 2-EH. System 10 includes 2-EH reaction unit 102 and separation unit 104. 2-EH reaction unit 102 includes one or more aldolisation reactor(s), dehydration reactor(s), and dehydrogenation reactor(s). Separation unit 104 includes distillation units.

To produce 2-EH involves reacting, in 2-EH reaction unit 102, synthesis gas 100 with propylene 101 to produce intermediary products such as EHA and EPA, at least some of which is ultimately converted to 2-EH, as described above. The 2-EH is flowed from 2-EH reaction unit 102 as a part of crude alcohol 103. Based on the process carried out in 2-EH reaction unit 102, crude alcohol 103 may comprise 2-EH, EHA, EPA, butanol, heavies, and water. In system 10, separation unit 104 refines crude alcohol 103 by removing EHA, EPA, butanol, heavies, and water to produce 2-EH product 105, which typically has 99.7 mol. % 2-EH. Byproducts of the separation process in separation unit 104 include 2-EH & EHA stream 106, EPA & 2-EH stream 107, lights stream 108, and heavies stream 109. 2-EH & EHA stream 106 and EPA & 2-EH stream 107 are recycled to 2-EH reaction unit 102.

In system 10, a considerable quantity of 2-EH product that is produced is recycled back to 2-EH reaction unit 102. Because of this, there is high-energy consumption in 2-EH reaction unit 102 to control the reaction conditions. Improvements in this and other aspects of the production of 2-EH are desired.

BRIEF SUMMARY OF THE INVENTION

A method has been discovered for recovering 2-EH from crude alcohol. The discovered method involves refining a crude alcohol stream to form a high concentration 2-EH stream and byproduct streams. In the discovered method, the byproduct streams of the refining process are combined. Then the combined stream is refined to form additional 2-EH product.

Embodiments of the invention include a method of recovering 2-EH from a crude alcohol stream comprising (1) primarily 2-EH, (2) EPA, and (3) EHA. The method includes separating the crude alcohol stream into a first stream comprising primarily 2-EH, a second stream comprising primarily EPA and 2-EH collectively, and a third stream comprising primarily 2-EH and EHA collectively. The method further includes combining the second stream and the third stream to form a combined stream. Further yet, the method includes separating the combined stream to form a first product stream comprising primarily 2-EH and a second product stream comprising primarily 2-EH, EHA, and EPA collectively.

Embodiments of the invention include a method of recovering 2-EH from a crude alcohol stream comprising (1) primarily 2-EH, (2) EPA, and (3) EHA. The method includes reacting, in a reaction unit, synthesis gas and propylene to form the crude alcohol stream. The method also includes separating the crude alcohol stream into a first stream comprising primarily 2-EH, a second stream comprising primarily EPA and EH collectively, and a third stream comprising primarily EH and EHA collectively. The method further includes combining the second stream and the third stream to form a combined stream. Further yet, the method includes flowing the combined stream to a packed recovery distillation column and separating the combined stream, by the packed recovery distillation column, to form a bottom product stream comprising primarily 2-EH and a distillate product stream comprising primarily, 2-EH, EHA, and EPA collectively. The method also includes recycling the distillate product stream to the reaction unit and processing, in the reaction unit, EHA and EPA of the distillate product stream to produce 2-EH.

The following includes definitions of various terms and phrases used throughout this specification.

The terms "about" or "approximately" are defined as being close to as understood by one of ordinary skill in the art. In one non-limiting embodiment the terms are defined to be within 10%, preferably, within 5%, more preferably, within 1%, and most preferably, within 0.5%.

The terms "wt. %", "vol. %" or "mol. %" refer to a weight, volume, or molar percentage of a component, respectively, based on the total weight, the total volume, or the total moles of material that includes the component. In a non-limiting example, 10 moles of component in 100 moles of the material is 10 mol. % of component.

The term "substantially" and its variations are defined to include ranges within 10%, within 5%, within 1%, or within 0.5%.

The terms "inhibiting" or "reducing" or "preventing" or "avoiding" or any variation of these terms, when used in the claims and/or the specification, includes any measurable decrease or complete inhibition to achieve a desired result.

The term "effective," as that term is used in the specification and/or claims, means adequate to accomplish a desired, expected, or intended result.

The term "primarily," as that term is used in the specification and/or claims, means greater than any of 50 wt. %, 50 mol. %, or 50 vol. %. For example, "primarily" may include 50.1 wt. % to 100 wt. % and all values and ranges there between, 50.1 mol. % to 100 mol. % and all values and ranges there between, 50.1 vol. % to 100 vol. % and all values and ranges there between.

The use of the words "a" or "an" when used in conjunction with the term "comprising," "including," "containing," or "having" in the claims or the specification may mean "one," but it is also consistent with the meaning of "one or more," "at least one," and "one or more than one."

The words "comprising" (and any form of comprising, such as "comprise" and "comprises"), "having" (and any form of having, such as "have" and "has"), "including" (and any form of including, such as "includes" and "include") or "containing" (and any form of containing, such as "contains" and "contain") are inclusive or open-ended and do not exclude additional, unrecited elements or method steps.

The process of the present invention can "comprise," "consist essentially of," or "consist of" particular ingredients, components, compositions, etc., disclosed throughout the specification.

In the context of the present invention, at least fifteen embodiments are now described. Embodiment 1 is a method of recovering 2-ethyl hexanol (2-EH) from a crude alcohol stream containing (1) primarily 2-EH, (2) 2-ethyl, 3-propyl acrolein (EPA), and (3) 2-ethylhexanal (EHA). The method includes the steps of separating the crude alcohol stream into a first stream containing primarily 2-EH, a second stream containing primarily EPA and 2-EH collectively, and a third stream containing primarily 2-EH and EHA collectively; combining the second stream and the third stream to form a combined stream; and separating the combined stream to form a first product stream containing primarily 2-EH and a second product stream containing primarily, 2-EH, EHA, and EPA collectively. Embodiment 2 is the method of embodiment 1, further including the step of recycling the second product stream to a process that uses the EHA and the EPA of the second product stream to form additional 2-EH. Embodiment 3 is the method of any of embodiments 1 and 2, further including the step of flowing the combined stream to a distillation column, wherein the separating of the combined stream is carried out by the distillation column, wherein the first product stream is a bottom product stream and the second product stream is a distillate product stream. Embodiment 4 is the method of any of embodiments 1 to 3, wherein 70 to 95 mol. % of 2-EH in the combined stream is contained in the first product stream. Embodiment 5 is the method of any of embodiments 1 to 4, wherein the first product stream is greater than 95 mol. % 2-EH. Embodiment 6 is the method of any of embodiments 1 to 5, wherein the first product stream is greater than 99 mol. % 2-EH. Embodiment 7 is the method of any of embodiments 1 to 6, wherein the first product stream is 99.75 mol. % or greater of 2-EH. Embodiment 8 is the method of any of embodiments 3 to 7, wherein the distillation column is operated such that the first product stream is at a temperature in a range of 150 to 160° C. and a pressure in a range of 0.2 to 0.6 bars. Embodiment 9 is the method of any of embodiments 3 to 8, wherein the distillation column is operated such that the second product stream is at a temperature in a range of 205 to 215° C. and a pressure of 1.8 to 2.2 bars. Embodiment 10 is the method of any of embodiments 1 to 9, wherein the first product stream contains more 2-EH than the second product stream. Embodiment 11 is the method of any of embodiments 1 to 9, wherein a mass ratio of 2-EH in the first product stream to 2-EH in the second product stream is in a range of 1.2/1 to 1.6/1. Embodiment 12 is the method of any of embodiments 1 to 11, wherein the mass of 2-EH in the first product stream is 55% to 65% of the mass of 2-EH in the combined stream.

Embodiment 13 is a method of recovering 2-ethyl hexanol (2-EH) from a crude alcohol stream containing (1) primarily 2-EH, (2) 2-ethyl, 3-propyl acrolein (EPA), and (3) 2-ethylhexanal (EHA). The method includes the steps of reacting, in a reaction unit, synthesis gas and propylene to form the crude alcohol stream; separating the crude alcohol stream into a first stream containing primarily 2-EH, a second stream containing primarily EPA and EH collectively, and a third stream containing primarily EH and EHA collectively; combining the second stream and the third stream to form a combined stream; flowing the combined stream to a packed recovery distillation column; separating the combined stream, by the packed recovery distillation column, to form a bottom product stream containing primarily 2-EH and a distillate product stream containing primarily, 2-EH, EHA, and EPA collectively; and recycling the distillate product stream to the reaction unit; and processing, in the reaction unit, EHA and EPA of the distillate product stream to produce 2-EH. Embodiment 14 is the method of embodiment 13, wherein the packed recovery distillation column is operated such that the bottom product stream is at a temperature in a range of 150 to 160° C. and a pressure in a range of 0.2 to 0.6 bars. Embodiment 15 is the method of any of embodiments 13 and 14, wherein the packed recovery distillation column is operated such that the distillate product stream is at a temperature in a range of 205 to 215° C. and a pressure of 1.8 to 2.2 bars.

Other objects, features and advantages of the present invention will become apparent from the following figures, detailed description, and examples. It should be understood, however, that the figures, detailed description, and examples, while indicating specific embodiments of the invention, are given by way of illustration only and are not meant to be limiting. Additionally, it is contemplated that changes and modifications within the spirit and scope of the invention will become apparent to those skilled in the art from this detailed description. In further embodiments, features from specific embodiments may be combined with features from other embodiments. For example, features from one embodiment may be combined with features from any of the other embodiments. In further embodiments, additional features may be added to the specific embodiments described herein.

BRIEF DESCRIPTION OF THE DRAWINGS

For a more complete understanding, reference is now made to the following descriptions taken in conjunction with the accompanying drawings, in which.

DETAILED DESCRIPTION OF THE INVENTION

A method has been discovered for recovering 2-EH from a crude alcohol stream. The discovered method involves refining the crude alcohol stream to form concentrated 2-EH and byproduct streams (which also contain 2-EH, EPA and EHA), combining the byproduct streams of the refining process, and refining the combined stream to form additional 2-EH product. In embodiments of the invention, the byproduct streams do not have to be recycled as is but can be subjected to a recovery processes to recover additional 2-EH. For example, in embodiments of the invention, 70% of the existing 2-EH in what would be recycle streams in conventional processes is recovered. The recovery can be implemented by the use of a 2-EH recovery distillation column. Recovering the 2-EH product by the recovery distillation column, according to embodiments of the invention, helps improve the productivity and reduce the energy requirement in the reaction system.

Figure 1:
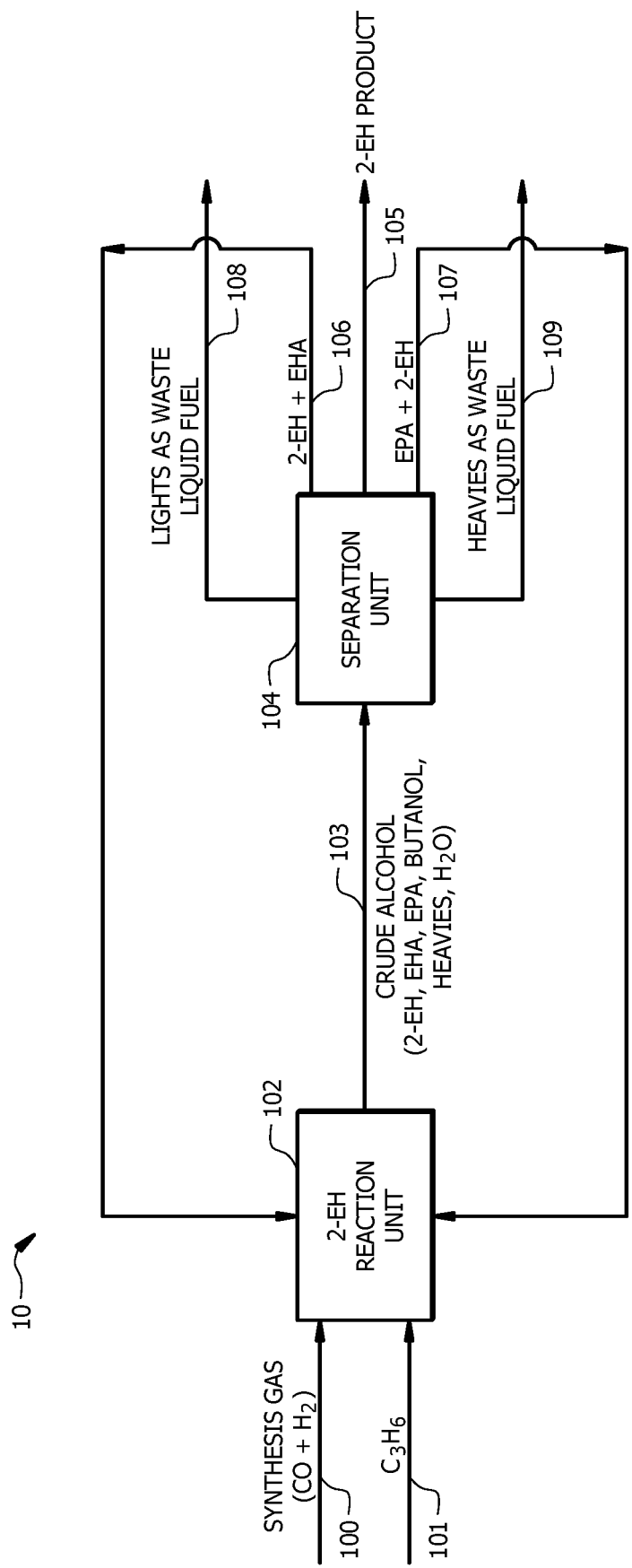
FIG. 1 shows a prior art system for producing 2-EH.
Figure 2:
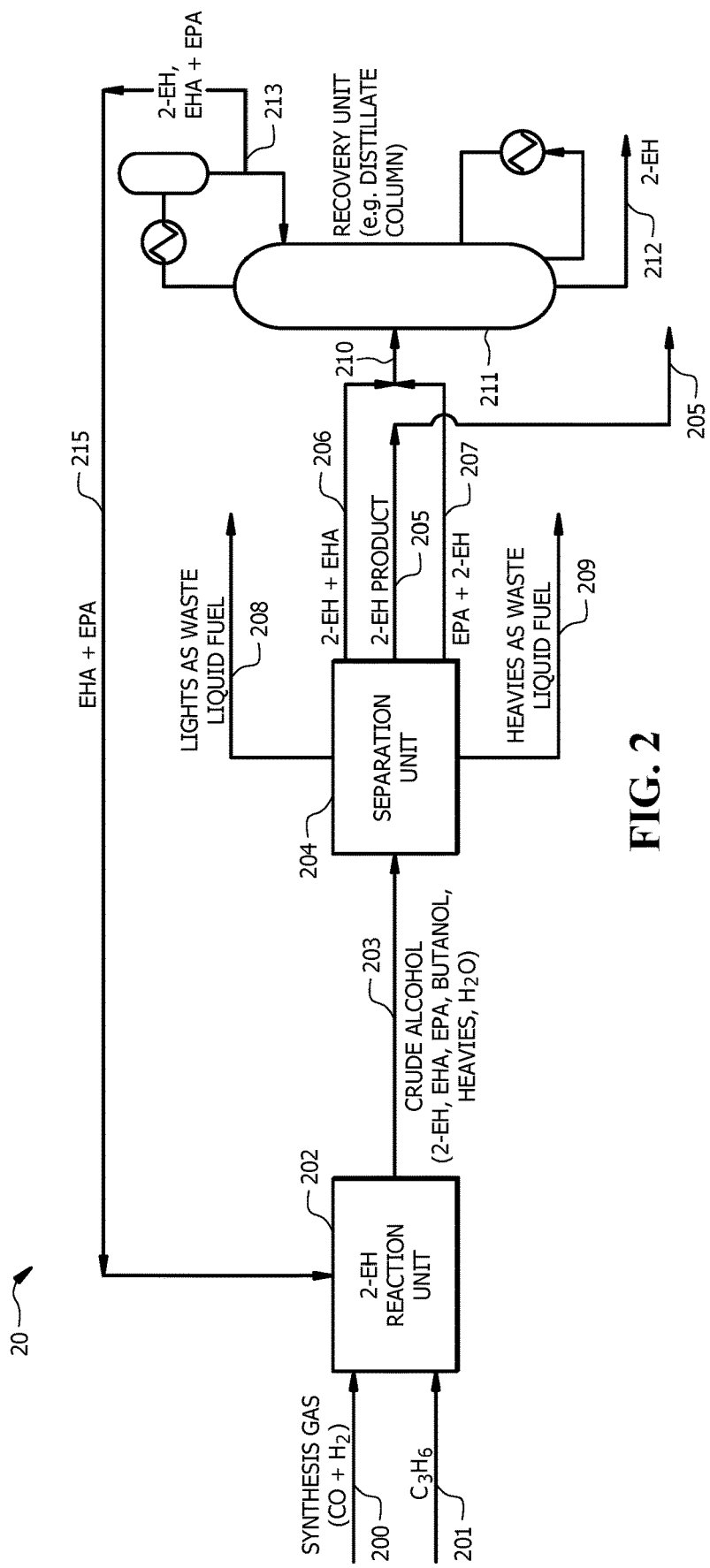
FIG. 2 shows a system of recovering 2-EH from a crude alcohol stream, according to embodiments of the invention.
Figure 3:
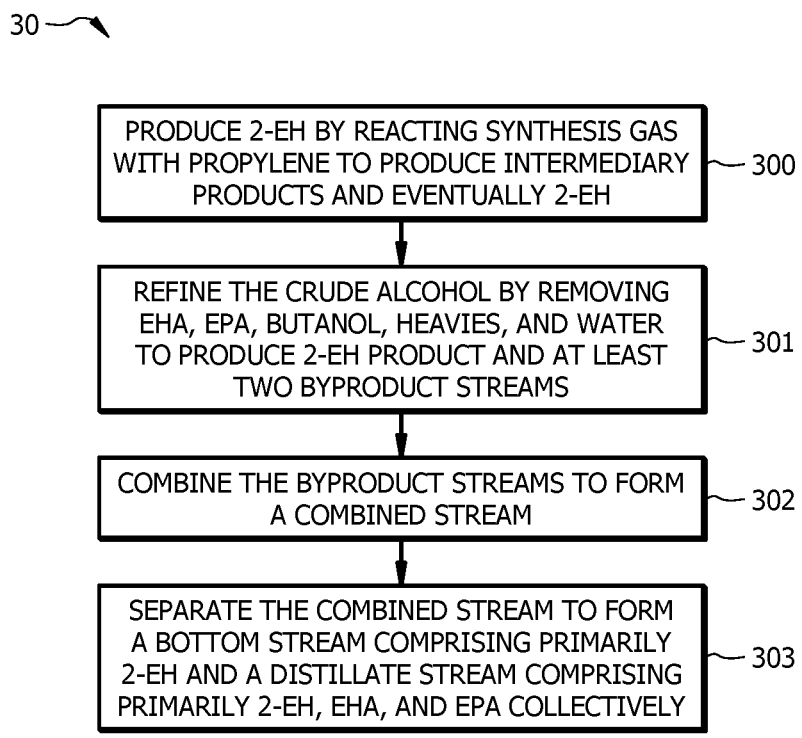
FIG. 3 shows a method of recovering 2-EH from a crude alcohol stream, according to embodiments of the invention.

FIG. 2 shows system 20 for recovering 2-EH from a crude alcohol stream, according to embodiments of the invention. FIG. 3 shows method 30 for recovering 2-EH from a crude alcohol stream, according to embodiments of the invention. Method 30 may be implemented by system 20.

System 20 includes 2-EH reaction unit 202, separation unit 204, and recovery unit 211. 2-EH reaction unit 202 may include one or more aldolisation reactor(s), dehydration reactor(s), and dehydrogenation reactor(s). Separation unit 204 may include one or more distillation unit(s). Recovery unit 211 may be a distillation column adapted to separate a stream that comprises 2-EH, EHA, and EPA to form a first stream comprising primarily 2-EH product and a second stream comprising primarily 2-EH, EHA, and EPA. In embodiments of the invention, recovery unit 211 is a packed recovery distillation column.

According to embodiments of the invention, method 30 begins at block 300, which may include producing 2-EH by reacting, in 2-EH reaction unit 202, synthesis gas 200 with propylene 201 to produce intermediary products and eventually 2-EH. Block 300 may first involve reacting synthesis gas and propylene to produce butyraldehyde. Second, the butyraldehyde may then be converted to 2-ethyl, 3-propyl acrolein (EPA) by simultaneous aldolisation and dehydration. Third, 2-EH can be produced by hydrogenation of EPA in two steps. In the first hydrogenation step, EPA can be partially hydrogenated to produce 2-ethylhexanal (EHA). In the second hydrogenation step, the EHA can be further hydrogenated to produce 2-EH in a crude alcohol product. The 2-EH may be flowed from 2-EH reaction unit 202 as a component of crude alcohol 203. Based on the process carried out in 2-EH reaction unit 202, crude alcohol 203 may comprise 2-EH, EHA, EPA, butanol, heavies, and water. Typically, crude alcohol 203 comprises 86 to 92 mol. % 2-EH, 0.2 to 1.2 mol. % EHA, 0.05 to 0.2 mol. % EPA, 1.5 to 4 mol. % butanol, 0.1 to 0.8 mol. % heavies, and 5 to 8 mol. % water. Method 30 may involve, at block 301, separation unit 204 refining crude alcohol 203 by removing EHA, EPA, butanol, heavies, and water to produce 2-EH product 205. Typically, 2-EH product 205 comprises 99.6 to 99.8 mol. % 2-EH, 0.002 to 0.006 mol. % EHA, and 0.0001 to 0.0002 mol. % EPA.

Byproduct streams of the separation of block 301 may include 2-EH & EHA stream 206, EPA & 2-EH stream 207, lights stream 208, and heavies stream 209. 2-EH & EHA stream 206 may comprise primarily 2-EH and EHA. Typically, 2-EH & EHA stream 206 comprises 90 to 94 mol. % 2-EH, and 5 to 9 mol. % EHA. EPA & 2-EH stream 207 may comprise primarily EPA and 2-EH. Typically, EPA & 2-EH stream 207 comprises 88 to 92 mol. % 2-EH and 8 to 12 mol. % EPA. According to embodiments of the invention, EH & EHA stream 206 and EPA & 2-EH stream 207 are combined to form combined stream 210, at block 302. Combined stream 210, according to embodiments of the invention, comprises 2-EH, EHA, and EPA.

Method 30 may involve, at block 303, separating combined stream 210 to form a bottom stream (first product stream 212 comprising primarily 2-EH) and a distillate stream (second product stream 213) comprising primarily 2-EH, EHA, and EPA collectively. In embodiments of the invention, a distillation column of recovery unit 211 is operated such that first product stream 212 is at a temperature in a range of 150 to 160° C. and a pressure in a range of 0.2 to 0.6 bars. In embodiments of the invention, a distillation column of recovery unit 211 is operated such that second product stream 213 is at a temperature in a range of 205 to 215° C. and a pressure of 1.8 to 2.2 bars.

According to embodiments of the invention, 70 to 95 mol. % of 2-EH in combined stream 210 is recovered and is comprised in first product stream 212. According to embodiments of the invention, the bottom stream (first product stream 212) is greater than 95 mol. % 2-EH. In embodiments of the invention, first product stream 212 comprises 95.0 to 99.9 mol. % 2-EH, including all values therein; e.g., 95, 96, 97, 98, 99, and ranges therein; e.g., 95.0 to 95.9 mol. %, 96.0 to 96.9 mol. %, 97.0 to 97.9 mol. %, 98.0 to 98.9 mol. %, 99.0 to 99.9 mol. %. Further, in particular embodiments of the invention, the bottom stream (first product stream 212) is greater than 99 mol. % 2-EH. In embodiments of the invention, first product stream 212 comprises 99.0 to 99.9 mol. % 2-EH and 1.0 to 0.1 mol. % EPA. In embodiments of the invention, second product stream 213 comprises 78 to 82 mol. % 2-EH and 4 to 8 mol. % EHA. Second product stream 213 may be recycled to 2-EH reaction unit 202 to form additional 2-EH.

In embodiments of the invention, first product stream 212 comprises more 2-EH than second product stream 213. In embodiments of the invention, a mass ratio of 2-EH in first product stream 212 to 2-EH in second product stream 213 is in a range of 1.2/1 to 1.6/1. Further, in embodiments of the invention, the mass of 2-EH in the first product stream is 55% to 65% of the mass of 2-EH in the combined stream.

Although embodiments of the present invention have been described with reference to blocks of FIG. 3, it should be appreciated that operation of the present invention is not limited to the particular blocks and/or the particular order of the blocks illustrated in FIG. 3. Accordingly, embodiments of the invention may provide functionality as described herein using various blocks in a sequence different than that of FIG. 3.

In sum, embodiments of the invention can do one or more of the following: improve 2-EH product quality, reduce propylene specific consumption, and reduce the energy consumed in the reaction system and for product separation.

As part of the disclosure of the present invention, a specific example is included below. The example is for illustrative purposes only and is not intended to limit the invention. Those of ordinary skill in the art will readily recognize parameters that can be changed or modified to yield essentially the same results.

Example

Simulation of 2-EH Recovery System of FIG. 2

Table 1 below shows the results of a simulation of 2-EH recovery using system 20 of FIG. 2. The simulation was carried out using the simulation package ASPEN PLUS®.

TABLE 1

| | | Equipment | | | |
| --- | --- | --- | --- | --- | --- |
| | | | | Recovery Column | |
| | Units | Separation Unit 204 2-EH & EHA stream 206 | Separation Unit 204 EPA & 2-EH stream 207 | second product stream 213 (distillate) | first product stream 212 (2-EH recovery) |
| Description | | | | | |
| Temperature | C. | 196.448655 | 170 | 209.4110662 | 154.1154088 |
| Pressure | bar | 1.44325 | 2 | 2.01325 | 0.41325 |
| Mole Flows | kmol/hr | 6.476274779 | 9.441228072 | 7.470583675 | 8.446919175 |
| Mole Fractions | | | | | |
| $H_2$ | | 0.00 | 0 | 0 | 0 |
| $N_2$ | | 0.00 | 0 | 0 | 0 |
| WATER | | 0.00 | 0 | 0 | 0 |
| N-BAL | | 0.00 | 0 | 0 | 0 |
| BUTANOL | | 0.00 | 0 | 0 | 0.00 |
| EPA | | 0.00 | 0.103354189 | 0.129126293 | 0.001319025 |
| EHA | | 0.071514111 | 0 | 0.061991413 | 3.91E−06 |
| EMPOH | | 0.006340111 | 0.000957201 | 0.005273409 | 0.001266972 |
| 2-EH | | 0.922145687 | 0.89568861 | 0.803608808 | 0.997410096 |
| $C_{16}$ RESID | | 0 | 0 | 0 | 0 |
| I-BAL | | 0.00 | 0 | 0 | 0 |
| Mass Flows | kg/hr | 0.00 | 1225.6 | 968.07366 | 1100 |
| $H_2$ | kg/hr | 0.00 | 0 | 0 | 0 |
| $N_2$ | kg/hr | 0.00 | 0 | 0 | 0 |
| WATER | kg/hr | 0.00 | 0 | 0 | 0 |
| N-BAL | kg/hr | 0.00 | 0 | 0 | 0 |
| BUTANOL | kg/hr | 4.22E−05 | 0 | 4.22E−05 | 0.00 |
| EPA | kg/hr | 1.90E−06 | 123.1433519 | 121.737287 | 1.406066549 |
| EHA | kg/hr | 59.38188106 | 0 | 59.3776508 | 0.004230135 |
| EMPOH | kg/hr | 5.347296356 | 1.176911492 | 5.130481188 | 1.393726652 |
| 2-EH | kg/hr | 777.7444385 | 1101.279737 | 781.8281988 | 1097.195977 |
| $C_{16}$ RESID | kg/hr | 0 | 0 | 0 | 0 |
| I-BAL | kg/hr | 1.78E−15 | 0 | 0 | 0 |

As evident in Table 1, the results show that recovery of a 2-EH stream of 99.7 mol. % is achievable in embodiments of the invention. Further, Table 1 shows that in embodiments of the invention, first product stream 212 comprises more 2-EH than second product stream 213. Further yet, Table 1 shows that, in embodiments of the invention, a mass ratio of 2-EH in first product stream 212 to 2-EH in second product stream 213 is approximately 1.4/1. Also, Table 1 shows that, in embodiments of the invention, the mass of 2-EH in first product stream 212 is 55% to 65% of the mass of 2-EH in combined stream 210 (2-EH & EHA stream 206 and EPA & 2-EH stream 207).

Although embodiments of the present application and their advantages have been described in detail, it should be understood that various changes, substitutions and alterations can be made herein without departing from the spirit and scope of the embodiments as defined by the appended claims. Moreover, the scope of the present application is not intended to be limited to the particular embodiments of the process, machine, manufacture, composition of matter, means, methods and steps described in the specification. As one of ordinary skill in the art will readily appreciate from the above disclosure, processes, machines, manufacture, compositions of matter, means, methods, or steps, presently existing or later to be developed that perform substantially the same function or achieve substantially the same result as the corresponding embodiments described herein may be utilized. Accordingly, the appended claims are intended to include within their scope such processes, machines, manufacture, compositions of matter, means, methods, or steps.

The invention claimed is:

1. A method of recovering 2-ethyl hexanol (2-EH) from a crude alcohol stream comprising (1) primarily 2-EH, (2) 2-ethyl, 3-propyl acrolein (EPA), and (3) 2-ethylhexanal (EHA), the method comprising:
    separating the crude alcohol stream into a first stream comprising primarily 2-EH, a second stream comprising primarily EPA and 2-EH collectively, and a third stream comprising primarily 2-EH and EHA collectively;
    combining the second stream and the third stream to form a combined stream; and
    separating the combined stream to form a first product stream comprising primarily 2-EH and a second product stream comprising primarily, 2-EH, EHA, and EPA collectively.

2. The method of claim 1, further comprising:
    recycling the second product stream to a process that uses the EHA and the EPA of the second product stream to form additional 2-EH.

3. The method of claim 1, further comprising:
flowing the combined stream to a distillation column, wherein the separating of the combined stream is carried out by the distillation column, wherein the first product stream is a bottom product stream and the second product stream is a distillate product stream.

4. The method of claim 1, wherein 70 to 95 mol. % of 2-EH in the combined stream is comprised in the first product stream.

5. The method of claim 1, wherein the first product stream is greater than 95 mol. % 2-EH.

6. The method of claim 1, wherein the first product stream is greater than 99 mol. % 2-EH.

7. The method of claim 1, wherein the first product stream is 99.75 mol. % or greater of 2-EH.

8. The method of claim 3, wherein the distillation column is operated such that the first product stream is at a temperature in a range of 150 to 160° C. and a pressure in a range of 0.2 to 0.6 bars.

9. The method of claim 3, wherein the distillation column is operated such that the second product stream is at a temperature in a range of 205 to 215° C. and a pressure of 1.8 to 2.2 bars.

10. The method of claim 1, wherein the first product stream comprises more 2-EH than the second product stream.

11. The method of claim 1, wherein a mass ratio of 2-EH in the first product stream to 2-EH in the second product stream is in a range of 1.2/1 to 1.6/1.

12. The method of claim 1, wherein the mass of 2-EH in the first product stream is 55% to 65% of the mass of 2-EH in the combined stream.

13. A method of recovering 2-ethyl hexanol (2-EH) from a crude alcohol stream comprising (1) primarily 2-EH, (2) 2-ethyl, 3-propyl acrolein (EPA), and (3) 2-ethylhexanal (EHA), the method comprising:
reacting, in a reaction unit, synthesis gas and propylene to form the crude alcohol stream;
separating the crude alcohol stream into a first stream comprising primarily 2-EH, a second stream comprising primarily EPA and EH collectively, and a third stream comprising primarily EH and EHA collectively;
combining the second stream and the third stream to form a combined stream;
flowing the combined stream to a packed recovery distillation column;
separating the combined stream, by the packed recovery distillation column, to form a bottom product stream comprising primarily 2-EH and a distillate product stream comprising primarily, 2-EH, EHA, and EPA collectively; and
recycling the distillate product stream to the reaction unit; and
processing, in the reaction unit, EHA and EPA of the distillate product stream to produce 2-EH.

14. The method of claim 13, wherein the packed recovery distillation column is operated such that the bottom product stream is at a temperature in a range of 150 to 160° C. and a pressure in a range of 0.2 to 0.6 bars.

15. The method of claim 13, wherein the packed recovery distillation column is operated such that the distillate product stream is at a temperature in a range of 205 to 215° C. and a pressure of 1.8 to 2.2 bars.

16. The method of claim 14, wherein the packed recovery distillation column is operated such that the distillate product stream is at a temperature in a range of 205 to 215° C. and a pressure of 1.8 to 2.2 bars.

17. The method of claim 2, further comprising the step of flowing the combined stream to a distillation column, wherein the separating of the combined stream is carried out by the distillation column, wherein the first product stream is a bottom product stream and the second product stream is a distillate product stream, wherein the first product stream is 99.75 mol. % or greater of 2-EH.

18. The method of claim 3, further comprising the step of flowing the combined stream to a distillation column, wherein the separating of the combined stream is carried out by the distillation column, wherein the first product stream is a bottom product stream and the second product stream is a distillate product stream, wherein the distillation column is operated such that the first product stream is at a temperature in a range of 150 to 160° C. and a pressure in a range of 0.2 to 0.6 bars.

19. The method of claim 3, wherein the distillation column is operated such that the second product stream is at a temperature in a range of 205 to 215° C. and a pressure of 1.8 to 2.2 bars.

20. The method of claim 2, wherein the first product stream comprises more 2-EH than the second product stream.

* * * * *